United States Patent [19]
Doumenis

[11] Patent Number: 4,776,839
[45] Date of Patent: Oct. 11, 1988

[54] THREE STAGE IMPLANTABLE PRESSURE RELIEF VALVE WITH IMPROVED VALVE STEM MEMBER
[75] Inventor: Demetrios Doumenis, Miami, Fla.
[73] Assignee: Cordis Corporation, Miami, Fla.
[21] Appl. No.: 922,080
[22] Filed: Oct. 21, 1986
[51] Int. Cl.⁴ .................................................. A61M 27/00
[52] U.S. Cl. ...................................... 604/9; 137/504; 137/508; 137/859; 604/247
[58] Field of Search ............... 137/504, 508, 510, 859; 138/45; 604/8-10, 247

[56] References Cited
U.S. PATENT DOCUMENTS

| | | | |
|---|---|---|---|
| 28,722 | 6/1860 | Whitacker | 137/508 |
| 79,436 | 6/1868 | Bechtel | 137/508 |
| 780,986 | 1/1905 | Francis | 137/504 |
| 1,139,455 | 5/1915 | Gase | 137/508 |
| 1,159,214 | 11/1915 | Gueux | 137/508 |
| 1,199,152 | 9/1916 | Bruce | 137/508 |
| 1,468,434 | 9/1923 | Zander | 137/504 |
| 2,207,382 | 7/1940 | McNamara | 277/21 |
| 2,290,151 | 7/1942 | McCollum | 237/12.3 |
| 2,969,066 | 1/1961 | Holter et al. | 128/350 |
| 3,109,429 | 11/1963 | Schwartz | 128/350 |
| 3,233,610 | 2/1966 | Wade | 128/350 |
| 3,270,771 | 9/1966 | Morgan | 137/525.3 |
| 3,288,142 | 11/1966 | Hakim | 128/350 |
| 3,308,798 | 3/1967 | Snider | 123/119 |
| 3,421,542 | 1/1969 | Adams et al. | 137/504 |
| 3,492,996 | 2/1970 | Fountain | 128/350 |
| 3,566,875 | 3/1971 | Stoehr | 128/350 |
| 3,601,128 | 8/1971 | Hakim | 128/350 |
| 3,654,932 | 4/1972 | Newkirk et al. | 128/350 V |
| 3,674,050 | 7/1972 | Kuffer et al. | 137/536 |
| 3,683,929 | 8/1972 | Holter | 128/350 V |
| 3,756,243 | 9/1973 | Schulte | 128/350 V |
| 3,768,508 | 10/1973 | Schulte | 137/522 |
| 3,769,982 | 11/1973 | Schulte | 128/350 |
| 3,782,410 | 1/1974 | Steuby | 137/496 |
| 3,804,113 | 4/1974 | Garcea | 137/496 |
| 3,827,439 | 8/1974 | Schulte et al. | 128/350 |
| 3,886,948 | 6/1975 | Hakim et al. | 128/350 |
| 3,889,687 | 6/1975 | Harris | 128/350 V |
| 3,901,245 | 8/1975 | Spitz et al. | 128/350 V |
| 3,924,635 | 12/1975 | Hakim | 128/350 V |
| 3,970,105 | 7/1976 | Pelton et al. | 137/498 |
| 3,985,140 | 10/1976 | Harris | 128/350 V |
| 3,991,768 | 11/1976 | Portnoy | 128/350 |
| 3,999,553 | 12/1976 | Spitz | 128/350 |
| 4,103,689 | 8/1978 | Leighton | 128/350 V |
| 4,106,510 | 8/1978 | Hakim et al. | 128/350 V |
| 4,156,422 | 5/1979 | Hildebrandt et al. | 128/748 |
| 4,167,952 | 9/1979 | Reiniecke | 137/493 |
| 4,215,695 | 8/1980 | Spitz et al. | 128/350 |
| 4,246,930 | 1/1981 | Bishop | 137/493.9 |
| 4,332,255 | 6/1982 | Hakim et al. | 128/350 |
| 4,340,038 | 7/1982 | McKean | 128/1.3 |
| 4,428,397 | 1/1984 | Bron | 137/504 |
| 4,437,493 | 3/1984 | Okuda et al. | 138/45 |
| 4,443,214 | 4/1984 | Marion | 604/9 |
| 4,451,128 | 5/1984 | Hakim et al. | 604/9 |
| 4,452,423 | 6/1984 | Bevlavi | 251/65 |
| 4,627,832 | 12/1986 | Hooven et al. | 137/508 |

FOREIGN PATENT DOCUMENTS 68509 8/1951 Netherlands.

Primary Examiner—Dalton L. Truluck
Attorney, Agent, or Firm—Lockwood, Alex, FitzGibbon & Cummings

[57] ABSTRACT

An implantable valve for controlling the passage of cerebrospinal fluid (CSF) from a ventricle of the brain to a suitable drainage location in the body includes a movable diaphragm responsive to pressure differentials between the ventricle and the drainage location. When the pressure differential is below a minimum threshold level, the valve is closed and CSF flow is prevented. When the pressure differential increases beyond the minimum threshold, the valve operates in a constant pressure mode to maintain a first predetermined CSF pressure differential across the valve. When the differential pressure increases beyond an intermediate threshold level, the valve operates in a constant flow mode to maintain a desired constant CSF flow rate through the valve. When the pressure differential increases beyond a maximum threshold level, the valve operates in a constant pressure mode to maintain a second predetermined CSF pressure differential across the valve. To provide for the various operating modes, the valve includes a valve stem and a valve closure member, which coact with a valve seat carried on the diaphragm. The valve stem is of an improved one-piece construction which can be readily fabricated using conventional manufacturing techniques.

8 Claims, 6 Drawing Sheets

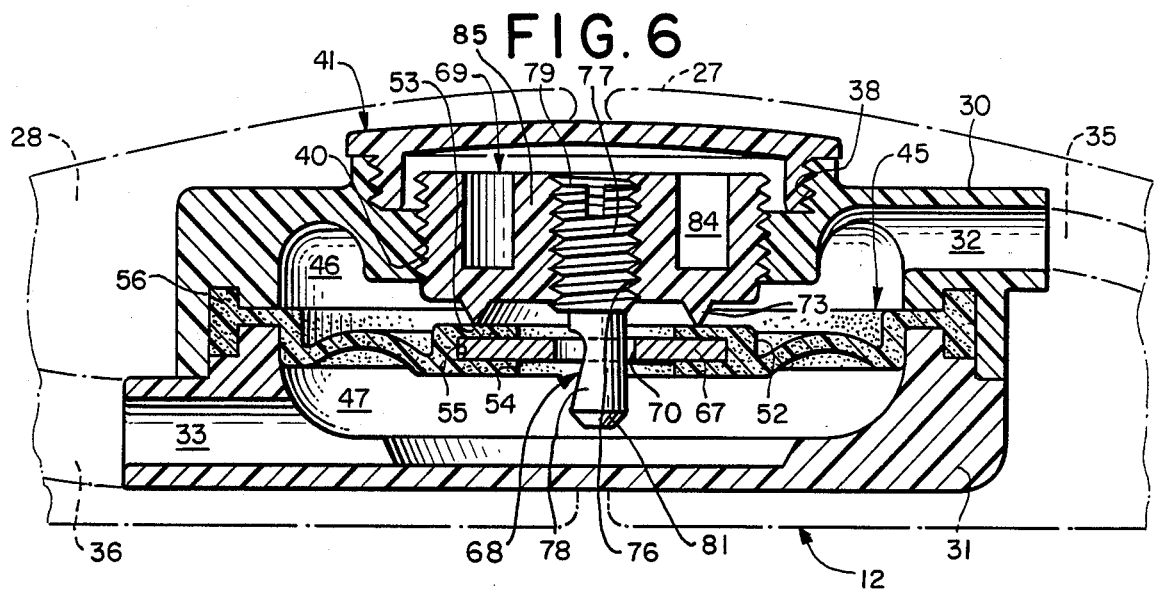

THREE STAGE IMPLANTABLE PRESSURE RELIEF VALVE WITH IMPROVED VALVE STEM MEMBER

BACKGROUND OF THE INVENTION

The present invention relates to an intracranial pressure relief valve and, more particularly, to a three stage CSF pressure relief valve having an adjustable valve closure member which establishes valve opening pressure, and an adjustable valve stem member of improved construction which establishes the pressure levels at which the valve transitions from a first constant pressure mode to a constant flow mode, an from the constant flow mode to a second constant pressure mode.

Hydrocephalus is a condition in which the body, for any one of a variety of reasons, is unable to relieve itself of excess cerebrospinal fluid (CSF) collected in the ventricles of the brain. The excessive collection of CSF in the ventricles results in an abnormal increase in epidural and intradural pressures, which may cause a number of adverse physiological effects including compression of the brain tissue, impairment of blood flow in the brain tissue, and impairment of the brain's normal metabolism.

Treatment of a hydrocephalic condition frequently involves relieving the abnormally high intracranial pressure. To this end, a variety of CSF pressure relief valves and methods of controlling CSF pressure have been developed which include various check valves, servo valves, or combinations thereof. Generally, such valves serve to divert CSF from the ventricles of the brain through a discharge line to a suitable drainage location in the body, such as the venous system or the peritoneal cavity, and, in their simplest form, operate by opening when the difference between CSF pressure and pressure in the discharge line exceeds a predetermined level.

The use of a simple check valve in the treatment of hydrocephalus is potentially disadvantageous since it is possible for such a valve to open in response to a sudden, but nevertheless perfectly normal, increases in differential pressure between CSF in the ventricular spaces and fluid at the drainage location, resulting in abnormal and potentially dangerous hyperdrainage of the ventricular spaces. For example, when a patient stands after lying in a recumbent position, the resulting increased vertical height of the fluid column existing between the head and the drainage location may result in such an increase in differential pressure. Accordingly, three stage CSF pressure relief valves, such as that described in the copending application of Christian Sainte-Rose and Michael D. Hooven, entiled "Three Stage Valve", Ser. No. 672,868, filed Nov. 19, 1984, now abandoned, have been developed which serve to prevent undesired hyperdrainage by limiting the flow rate of fluid through the valve when a sudden increase in differential pressure occurs.

In a valve of preferred construction incorporating the present invention a diaphragm is movable in response to the pressure differential between ventricular CSF pressure in an inlet chamber on one side of the diaphragm, and the pressure of fluid at the drainage location in an outlet chamber on the other side of the diaphragm. The diaphragm includes a valve seat which is mounted concentrically thereon and which includes a fluid metering orifice. The diaphragm is arranged to engage an adjustable valve closure member in the inlet chamber so as to close the valve when the pressure differential falls below a predetermined minimum level. A valve stem of generally cylindrical form having a fluid metering notch on the exterior surface thereof extends through the orifice to provide in cooperation with the orifice fluid metering between the two chambers.

The motion of the diaphragm in response to changes in differential pressure between the two valve chambers causes the valve to progress through four valving conditions. In the first valving condition, the diaphragm engages the valve closure member to prevent fluid flow through the valve. In the second valving condition, when the pressure differential between the two chambers exceeds a minimum threshold level, fluid flow between the chambers is regulated by coaction between the valve seat and the valve stem to maintain a first predetermined pressure level in the inlet chamber. In the third valving condition, which occurs in response to a sudden further increase in differential pressure beyond a further threshold level, such as might be caused by a drastic change in the position of the patient, such as movement from a recumbent position to a vertical position, the valve seat and valve stem coact to maintain a substantially constant flow rate. In the fourth valving condition, where the pressure differential increases still further and exceeds a maximum threshold level, the valve seat and valve stem coact to maintain a second predetermined pressure level in the first chamber to prevent hyperdrainage.

A CSF pressure relief valve is typically miniaturized for implantation and is required to perform with a high degree of precision under highly demanding conditions throughout a rather extensive, ever-changing mode of operation. Consequently, it has been necessary to carefully control the dimensions of the various parts of the valve, particularly the valve seat, the valve stem and the orifice defined by the valve seat. The parts involved are quite small, and working tolerances on the order of 0.0001 of an inch must be met. Considerable difficulty may be incurred in manufacturing such a valve, and it is to the reduction of this manufacturing difficulty that the construction of the present invention is directed.

A CSF pressure relief valve incorporating a one piece valve stem is described in U.S. Pat. No. 4,627,832 entitled "Three Stage Intracranial Pressure Relief Valve Having Single Piece Valve Stem", which issued to Michael D. Hooven et al. on Dec. 9, 1986. Alternative constructions for the valve members are described in the copending application of Michael D. Hooven, entitled "Three Stage Intracranial Pressure Control Valve", Ser. No. 812,779, filed Dec. 23, 1985, now U.S. Pat. No. 4,714,459 issued Dec. 22, 1987, and in the copending application of Demetrios Doumenis, entitled Three Stage Implantable Pressure Relief Valve with Adjustable Valve Stem Member", Ser. No. 812,780, filed Dec. 23, 1985, now U.S. Pat. No. 4,729,672, issued Mar. 8, 1988.

The present invention is directed to an improvement in multi-stage CSF valve construction, and particularly in the valve stem of such a valve. Basically, this improvement utilizes an improved cylindrical construction for the valve stem wherein flow variations are achieved upon movement of the valve seat by the provision of a flow metering notch in the side wall of the valve stem, which allows the valve stem to be readily formed with great precision by conventional manufacturing techniques.

In view of the foregoing, it is a general object of the present invention to provide a new and improved valve for relieving intracranial pressure caused by the presence of excess CSF in the ventricles of the brain.

It is a more specific object of the present invention to provide a CSF pressure relief valve which can be more easily and economically manufactured.

It is a still more specific object of the present invention to provide a CSF pressure relief valve utilizing a one-piece valve stem of improved construction which may be more easily manufactured with high precision using conventional manufacturing techniques.

SUMMARY OF THE INVENTION

A valve for controlling the passage of body fluids from one location in the body to another location includes a housing having first and second interior chambers, inlet port means for establishing fluid communication between the first chamber and the one location, and outlet port means for establishing fluid communication between the second chamber and the other location. Partition means in the housing separate the first and second chambers and are movable in response to the fluid pressure differential therebetween. A valve seat forming part of the partition means and defining a fluid flow orifice are provided to permit flow of fluid between said chambers. A valve stem in the housing extends through the orifice to control fluid flow therethrough, the valve stem being generally cylindrical in form and including a metering notch for controlling fluid flow through the orifice.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 6 is an enlarged cross-sectional view of the pressure relief valve taken along lines 6—6 of FIG. 5 showing the valve in a closed condition.

FIG. 7 is a cross-sectional view, similar to FIG. 6, showing the pressure relief valve in a first constant pressure valving condition.

FIG. 8 is a cross-sectional view, similar to FIG. 6, showing the pressure relief valve in a constant flow rate valving condition.

FIG. 9 is a cross-sectional view, similar to FIG. 6, showing the pressure relief valve in a second constant pressure valving condition.

DESCRIPTION OF THE PREFERRED EMBODIMENT

Figure 1:
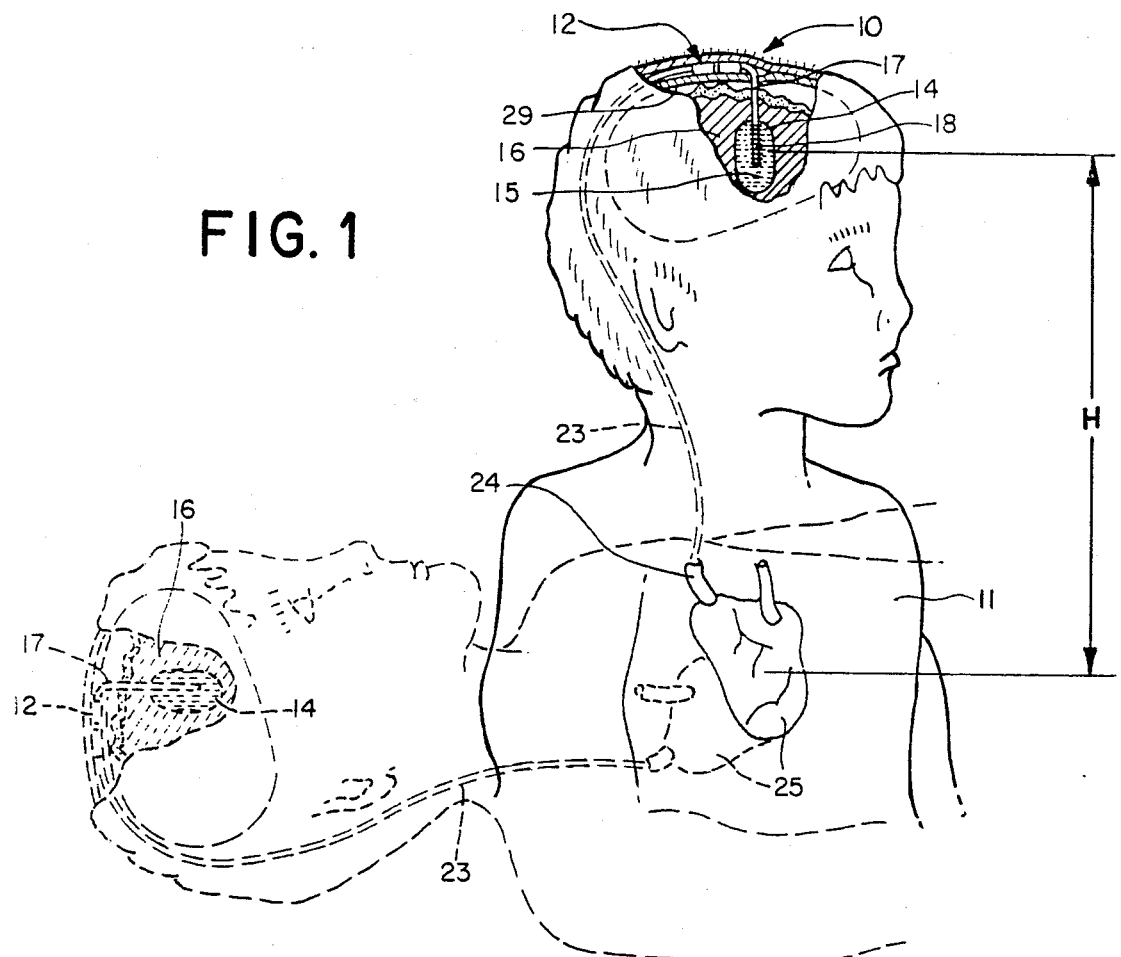
FIG. 1 is a perspective view, partially in section, of a CSF pressure relief system employing a three stage pressure regulator valve constructed in accordance with the present invention, showing such a system implanted within a patient.
Figure 2:
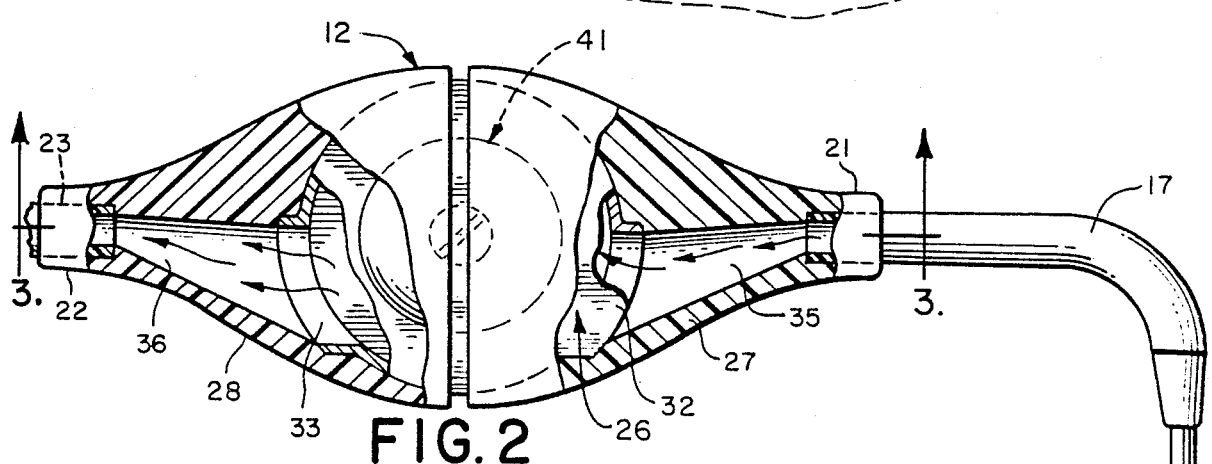
FIG. 2 is a plan view, partially in section, of the pressure relief valve showing the principal elements thereof.
Figure 3:
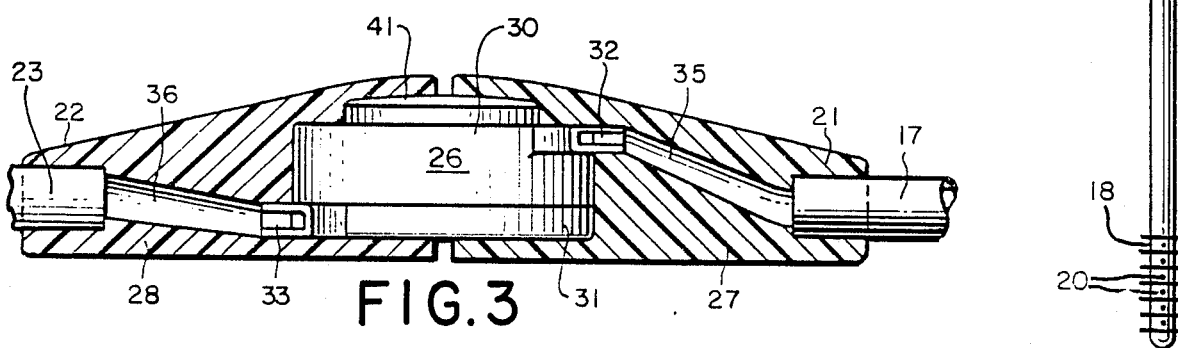
FIG. 3 is a cross-sectional view of the pressure relief valve taken along line 3—3 of FIG. 2.

Referring to the drawings, and particularly to FIGS. 1-3, a CSF pressure relief system 10 for maintaining a desired predetermined intracranial pressure in a patient 11 is illustrated. The system shown includes a three stage pressure relief valve 12 constructed in accordance with the present invention for controlling intracranial pressure.

Cerebrospinal fluid (CSF) 14 is drained from a ventricle 15 of the brain 16 by means of a ventricular catheter 17. Preferably, the catheter is radio-opaque in order to facilitate its accurate placement in the brain. The distal end 18 of the catheter may be provided with a plurality of apertures 20 (FIG. 2) for allowing the passage of CSF therethrough and is positioned in a suitable brain ventricle as illustrated. The other end of the catheter is coupled to the inlet port 21 of the valve to establish fluid communication between the valve and the ventricle. The outlet port 22 of the valve is attached to one end of a drain catheter 23, the opposite end of which discharges into an appropriate location in the patient's body. Although the drain catheter is shown threaded through a vein 24 to terminate within the right atrium of the patient's heart 25, a different drainage location, such as, for example, the peritoneal cavity, can be utilized instead. When open, the pressure relief valve 12 allows passage of CSF from the drain ventricle to the selected discharge location to relieve excessive intracranial pressure caused by excessive accumulation of CSF. Typically, means are provided for adjusting the pressure threshold at which the valve opens to suit the specific requirements of an individual patient.

While an increased intracranial pressure may result from the excessive accumulation of CSF in the brain ventricle, such an increase might also be a normal response to ordinary physical activity. For example, when a patient stands after lying for some time in a recumbent position, as illustrated in phantom in FIG. 1, intracranial pressure will suddenly increase by reason of the sudden increase in the vertical height H of the fluid column existing between the distal end of the ventricular catheter and the drainage location. If the relief valve were to open and permit unrestrained fluid flow in response to this pressure increase, hyperdrainage of the ventricle and brain hematoma could result. Accordingly, it is desirable that a CSF pressure relief valve include means for preventing such unrestricted fluid flow to the drainage location in the event of a sudden increase in intracranial pressure. The present three stage valve construction, by reason of providing three distinct valving conditions, in addition to a low pressure cut-off condition, provides protection against such sudden pressure increases, as well as other intracranial pressure variations which may be encountered in a patient.

The internal construction and operation of the three stage valve of the invention may best be understood by reference to FIGS. 2-6. As illustrated, the valve includes a generally disc-shaped inner housing 26 fashioned from a durable, biologically compatible material, such as thermoplastic polymers of polyethersulfone or polycarbonates. The inner housing 26 is received within an outer housing comprising two members 27 and 28 formed of silicone rubber or a similar material bonded together over the inner housing. The dimensions of the inner and outer housings are selected so as to be compatible with subcutaneous implantation of the valve over the cranium 29 (FIG. 1).

Figure 4:
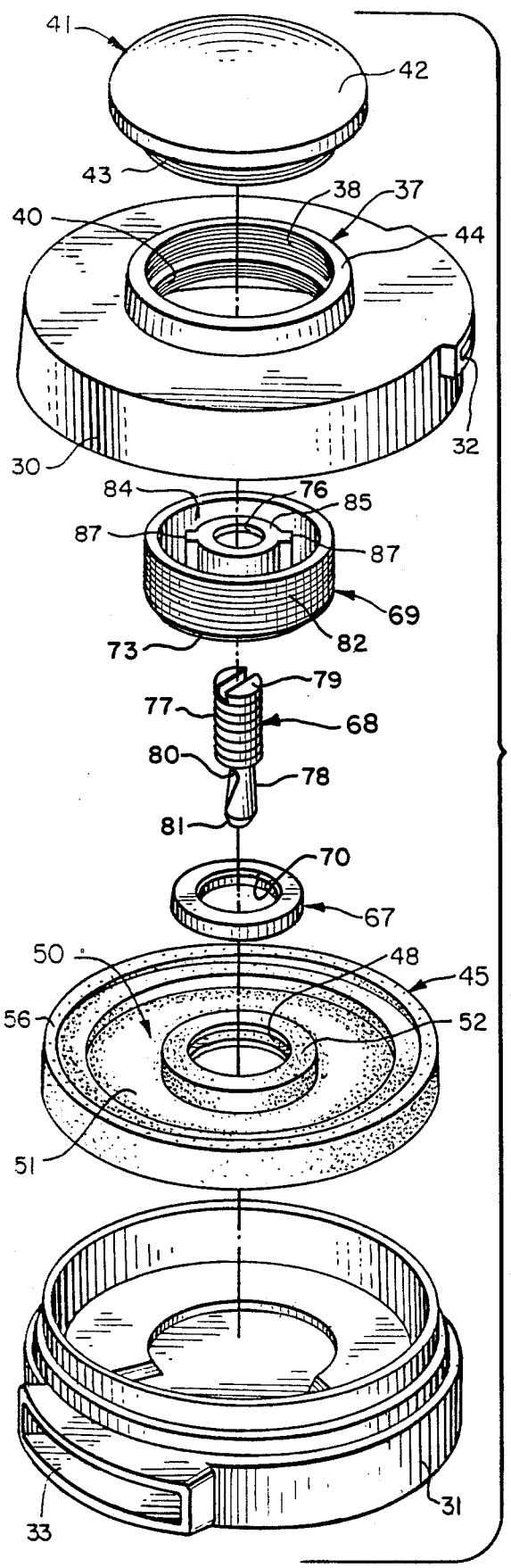
FIG. 4 is an exploded perspective view of the pressure relief valve showing the principal elements of the valve.
Figure 5:
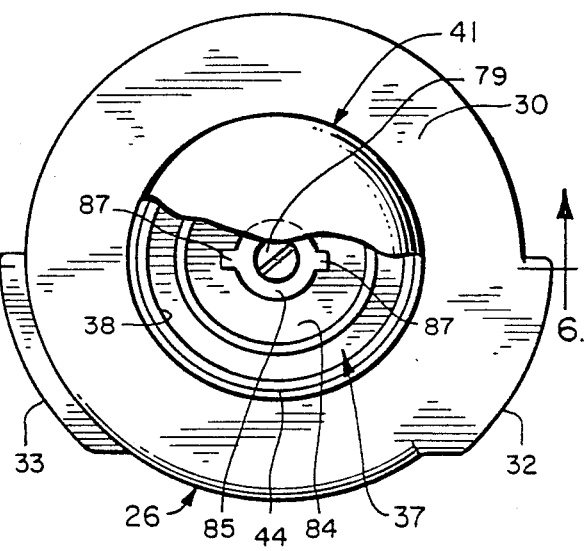
FIG. 5 is a top plan view, partially in section, of the pressure relief valve shown in FIGS. 1-4.

As is best illustrated in FIGS. 3 and 4, the inner housing 26 comprises two circular cup-shaped housing members 30 and 31. Housing member 30 includes an inlet port 32, and housing member 31 includes an outlet port 33, by means of which fluid can pass to or from the interior of the housing. In this regard, outer housing members 27 and 28 are provided with internal conduits 35 and 36, which provide fluid communication between inlet port 32 and outlet port 33, respectively.

Housing member 30 is provided with an aperture 37 through the upper surface thereof. As illustrated in FIG. 4, the aperture 37 includes a region 38 of relatively larger diameter coaxially aligned above a region of relatively smaller diameter 40. Both the relatively larger diameter and smaller diameter regions of the aperture are internally threaded as illustrated in order to seal the aperture while still allowing ready access to the interior region of the housing. The upper housing member 30 includes a removable cap 41 having a domed upper surface 42 and an externally threaded cylindrical lower portion 43 dimensioned to engage the threads of region 38 of aperture 37. To provide a tight seal between the cap and the housing, the upper housing member may include a raised annular seat 44 adjacent the periphery of the aperture against which the cap bears as it is turned into the upper housing member.

Referring to FIGS. 4 and 6, pressure relief valve 12 includes partition means in the form of a diaphragm 45 which extends laterally across the interior region of the inner housing to divide that region into first and second interior chambers 46 and 47 (FIG. 6), respectively. The diaphragm 45 may be fashioned from a flexible biocompatible material, such as silicone rubber, and, as best seen in FIG. 4, may comprise a disc-shaped member having an aperture 48 provided centrally therethrough. The operative region 50 of the diaphragm is provided with an annular groove 51 concentrically aligned with the center aperture which allows the operative region to travel vertically in response to differences between the first and second interior chambers.

Toward its center, and in the region immediately surrounding the aperture, the thickness of diaphragm 45 is increased to form a hub region 52, having upper and lower portions 53 and 54, respectively. An annular channel 55 of rectangular cross-section is provided in the sidewall of aperture 48 between portions 53 and 54. Diaphragm 45 also includes an integrally formed rim portion 56 along its outer circumference which facilitates installation of the diaphragm in the housing.

When assembled, upper housing member 30 interlocks with lower housing member 31 by engagement of their corresponding edges. Diaphragm 45 is received in a space provided therebetween with its rim portion fixedly engaged by the two interior housing members. When mounted in this manner, the operative portion 50 of the diaphragm is free to move in response to a pressure differential existing between fluids contained in the first and second chambers.

To regulate the passage of fluids from the first chamber 46 to the second chamber 47, and hence from a brain ventricle to the drainage area of the body, the valve includes valving means for regulating fluid communication between the first and second chambers. These valving means include a valve seat 67 mounted for movement with diaphragm 45, a valve stem 68 mounted to coact with the valve seat, and a valve closure member 69 mounted to coact with the diaphragm.

Referring to FIGS. 4 and 6, the valve seat 67 is preferably in the form of a washer-shaped ring dimensioned to fit within the annular channel 55 provided in the central hub portion 52 of diaphragm 45, between portions 53 and 54. The valve seat defines a flow metering orifice 70 extending centrally through the diaphragm for establisheing fluid communication between chambers 46 and 47. The diameter of the orifice is greater than the flow metering portion of the valve stem assembly 68, which extends through the orifice 70 of valve seat 67 as illustrated in FIG. 6. The valve seat is located directly beneath the valve stem so that a substantial part of the stem projects through orifice 70 during operation of the valve.

The valve closure member 69 is seen to be of generally cylindrical form, having an annular valving portion 73 arranged to bear against hub portion 52 of diaphragm 45. Closure member 69 is provided with an internally threaded aperture 76 adapted to receive valve stem member 68, the latter being provided with a threaded shank portion 77 which is threadedly received within the aperture. The valve stem 68 further includes an intermediate fluid metering portion 78, a slotted head portion 79, and a frusto-conical end portion 81. The slotted head portion 79 is adapted to receive a suitable tool to threadedly advance or retract valve stem 68 through valve closure member 69.

As seen in FIG. 6, in an assembled condition, the valve stem 68 is threaded through the central aperture 76 of valve closure member 69. The fluid flow control portion 78 of the stem extends below the plane of the annular valving portion 73 of valve closure member 69, and the upper slotted head portion 79 of the stem member projects upwardly from the top surface of the closure member. The head portion 79 is accessible when the cap 41 is removed from the valve to permit the use of a suitable tool to advance or retract the stem member 68 relative to the closure member 69, thus permitting adjustment of the pressure and flow levels maintained by stem member 68 in conjunction with valve seat 67.

The valve closure member 69 is mounted within the lesser diameter portion 40 of aperture 37. To this end, the outer surface 82 (FIG. 4) of closure member 69 is externally threaded and dimensioned to engage the threads of portion 40. The closure member 69 may include a raised centrally located stem mounting portion 85 which includes aperture 76 through which the head portion 79 of valve stem 68 extends. The mounting portion 85 may also include a pair of opposed outwardly projecting lugs or ears 87 which can be engaged by a suitable tool received in an adjacent annular recess 84 so that the closure member 69 can be threadedly advanced or retracted within the upper housing member 30 relative to diaphragm 45 and valve seat 67 to adjust the closing pressure of the valve.

When no differential pressure acts on diaphragm 45, the top surface of the diaphragm contacts the annular flow control portion 73 of valve closure member 69 and flow between chambers 46 and 47 is prevented. Adjustment of the pressure at which the valve opens is obtained by advancing or retracting valve closure member 69 within upper housing 30 relative to diaphragm 45. As the flow control portion 78 of the valve stem member 68 is received through the orifice 70 of valve seat 67, the sidewalls of the orifice additionally function as a guide for the stem member to alleviate sticking problems between the stem and the valve seat due to the lack of concentricity. This nesting configuration thus aids in reducing cost of manufacture as well as permitting increased variation in functional characteristics of the valve.

Figure 10:
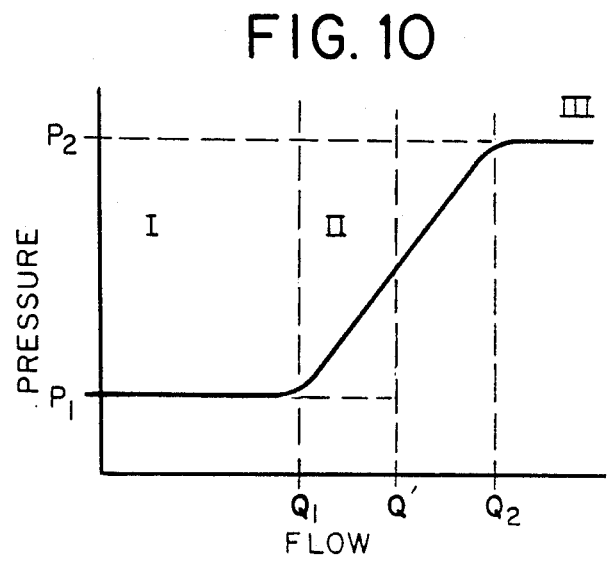
FIG. 10 is a simplified graphical depiction of certain pressure and flow characteristics of the three stage pressure relief valve useful in understanding the operation thereof.
Figure 11:
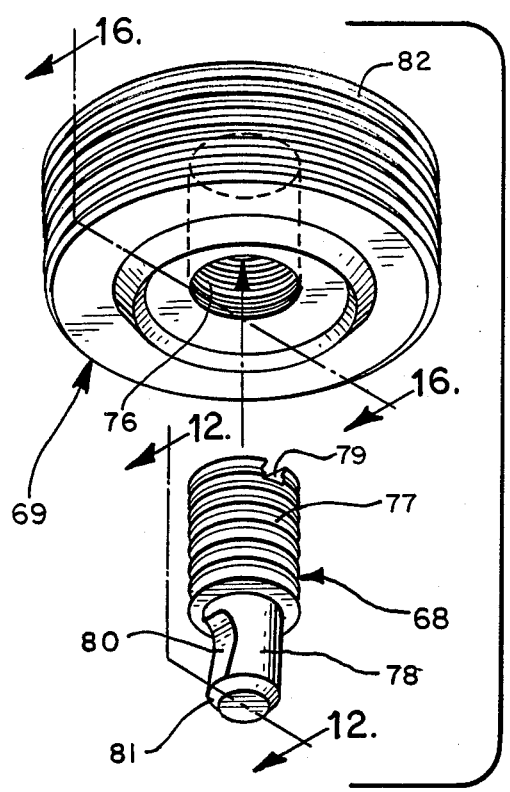
FIG. 11 is an enlarged exploded perspective view of the valve closure and valve stem members of the pressure relief valve.

FIG. 6 illustrates the operation of the valve in the absence of a CSF pressure differential, or a less than minimum threshold or popping pressure, between chambers 46 and 47. FIGS. 7-9 illustrate the operation of the valve in response to various CSF pressure levels in excess of the minimum threshold pressure. FIG. 10 is a simplified graphical depiction of pressure vs. flow characteristics of the valve. Basically, once CSF pressure has exceeded a predetermined minimum level the pressure relief valve 12 operates to maintain a predetermined differential pressure $P_1$ between fluid in the brain ventricle and fluid at the body drain location. The valve accomplishes this by adjusting the fluid flow rate Q through the valve so that the pressure $P_1$ is maintained. This operation of the valve is shown in region I of FIG. 10.

Should the differential pressure rapidly increase beyond a predetermined intermediate threshold level, such as when the patient stands, a CSF flow rate greater than a preselected maximum rate $Q_1$ would be necessary to maintain the desired pressure $P_1$. Since such a high flow rate would create the risk of hyperdrainage of the brain ventricle, the valve functions to maintain a relatively constant flow rate notwithstanding the increase in differential pressure, as depicted in region II of FIG. 10.

In a practical valve, the flow rate will not be entirely independent of the applied differential pressure but rather will increase from a lower flow rate $Q_1$ to a higher flow rate $Q_2$ as differential pressure increases between pressure $P_1$ and pressure $P_2$, as indicated by the solid line in FIG. 10. However, flow rates $Q_1$ and $Q_2$ are sufficiently low so that during a temporary rapid increase in differential pressure, pressure will return to normal before a quantity of CSF sufficient to cause adverse side effects flows through the valve. In a typical valve $Q_1$ and $Q_2$ may be 0.4 ml./min. and 0.8 ml./min., respectively, while pressures $P_1$ and $P_2$ may be 80 and 350 mm. of water, respectively.

While it is desirable to avoid high flow rates through the valve in order to avoid hyperdrainage of the ventricle, it may, under certain emergency conditions, be desirable to allow rapid shunting of CSF in order to avoid possible brain damage. When the valve is operating in region II, increases in differential pressure tend to close the valve. To avoid the possibility of building excessively high ventricular CSF pressure, the valve functions such that when differential pressure exceeds a maximum threshold level $P_2$, a fluid flow rate sufficient to maintain $P_2$ is established. This operation is depicted in Region III of FIG. 10. When the valve is operating in this region, further increases in differential pressure result in an increase in fluid flow through the valve, thereby stabilizing the pressure at slightly above $P_2$.

FIGS. 6-9 illustrate operation of the valve in the regions previously described. CSF applied to the inlet port 21 of the valve completely fills the first chamber 46 and exerts a downwardly directed force on the diaphragm 45 by reason of the CSF pressure within the brain ventricle. Since the second chamber 47 is in fluid communication with the selected drainage location in the body, the pressure of the CSF therein exerts an upwardly directed force on the lower surface of the diaphragm. Accordingly, the differential pressure between CSF in the brain ventricle and fluid at the drainage location results in vertical deflection of both the diaphragm and the valve seat 67 carried thereon.

As shown in FIG. 6, when differential pressure is negative or non-existent, or below the minimum threshold level of the valve, valve seat 67 contacts the annular valving portion 73 of valve closure member 69 and flow through orifice 70 is prevented. As shown in FIG. 7, when the differential pressure is relatively low but in excess of the threshold pressure resulting from the biasing of diaphragm 45 against valving portion 73, a slight downward displacement of the diaphragm occurs sufficient to displace valve seat 67 from the valving portion 73, thereby allowing CSF to pass through orifice 70 from chamber 46 to 47. As the pressure increases, the displacement of the diaphragm increases, causing a flow increase. Thus, the valve maintains a predetermined pressure differential $P_1$, as called for in Region I operation.

The bottom portion 78 of valve stem 68, which defines the fluid flow control and restrictor portion 78, is dimensioned so as to barely pass through the orifice 70 of valve seat 67. By way of example, in one embodiment of the valve, the valve seat orifice has a diameter of 0.040 inches at its narrowest point and the clearance between the restrictor portion of the valve stem and the orifice at the narrowest point is on the order of 0.001 of an inch.

Figure 12:
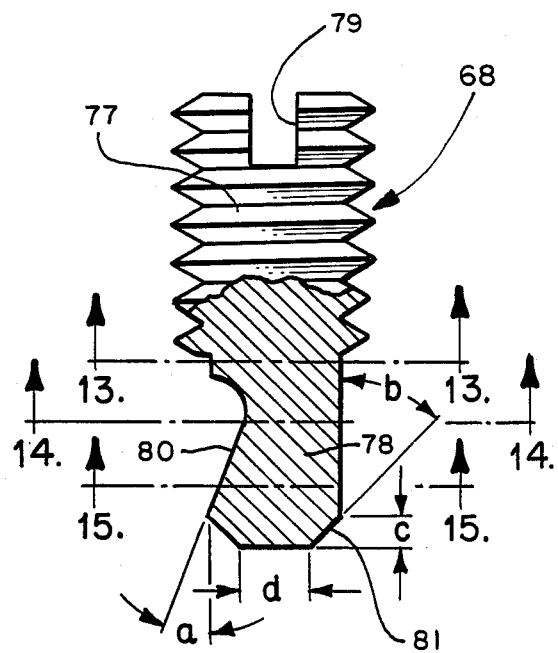
FIG. 12 is a cross-sectional view of the valve stem member of the pressure relief valve taken along line 12—12 of FIG. 11.
Figure 13:
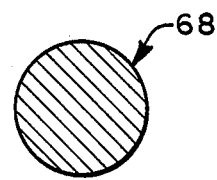
FIG. 13 is a cross-sectional view of the valve stem member taken along line 13—13 of FIG. 12.

As illustrated in FIGS. 11-15, the flow control portion 78 of the valve stem member 68 is, in accordance with the invention, generally cylindrical and includes a metering notch 80 of progressively reduced depth in the direction of fluid flow. As shown in FIG. 12, the notch 80 may be formed at an angle "a" relative to the axis of the stem, thereby providing the progressively decreasing depth. The frusto-conical end portion 81 is formed on the stem by an annular rim portion inclined at an angle "b" to the axis to provide a flat end surface of reduced diameter "d".

Figure 14:
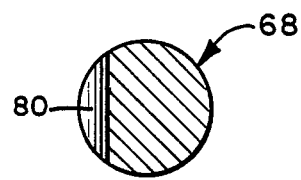
FIG. 14 is a cross-sectional view of the valve stem member taken along line 14—14 of FIG. 12.
Figure 15:
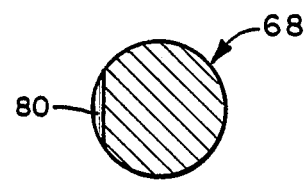
FIG. 15 is a cross-sectional view of the valve stem member taken along line 15—15 of FIG. 12.
Figure 16:
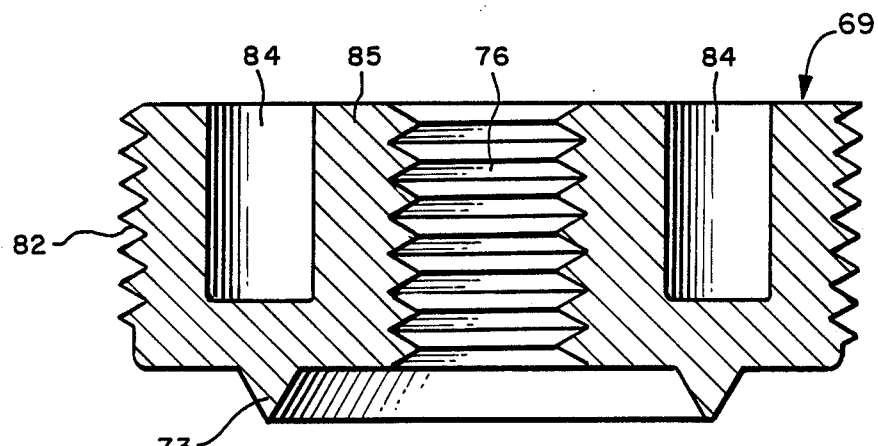
FIG. 16 is a cross-sectional view of the valve closure member of the pressure relief valve taken along line 16—16 of FIG. 11.
Figure 17:
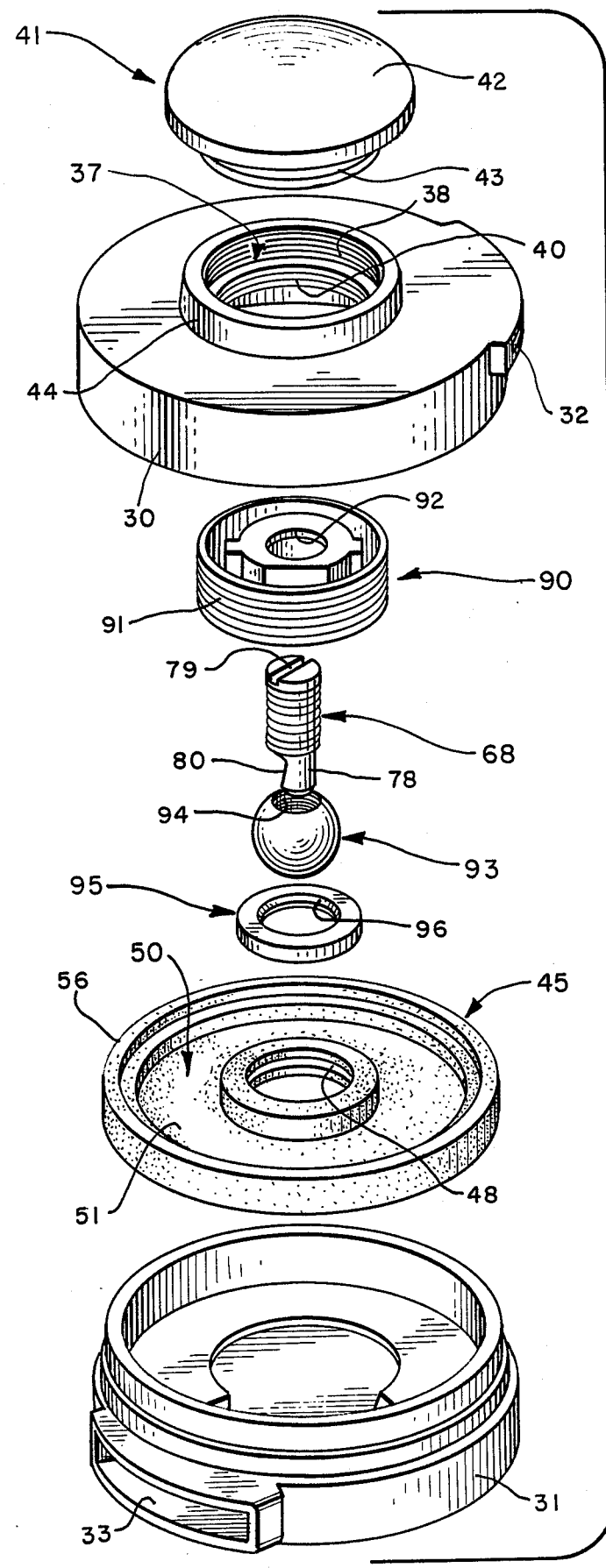
FIG. 17 is an exploded perspective view of the pressure relief valve showing an alternative construction for the valve closure member.
Figure 18:
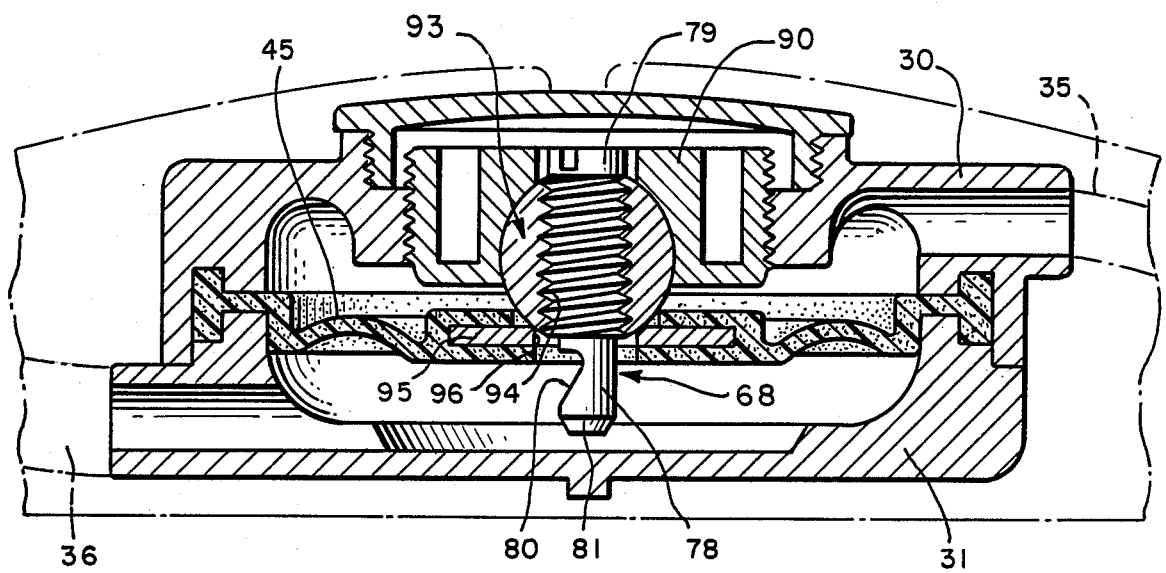
FIG. 18 is an enlarged cross-sectional view of the pressure relief valve of FIG. 17 showing the valve in a closed condition.
Figure 19:
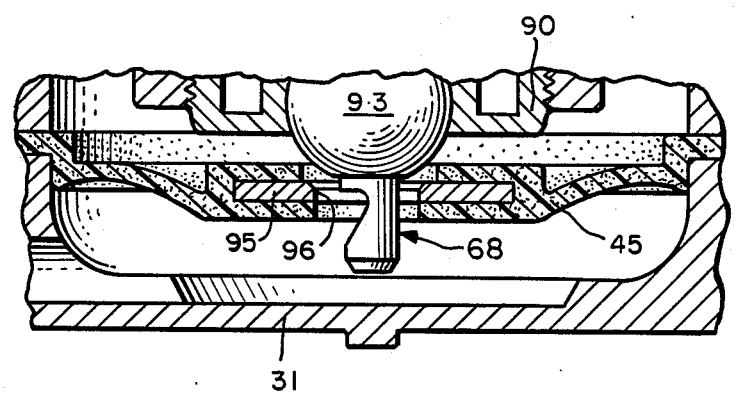
FIG. 19 is a cross-sectional view, similar to FIG. 18, showing the valve in a first constant pressure valving condition.
Figure 20:
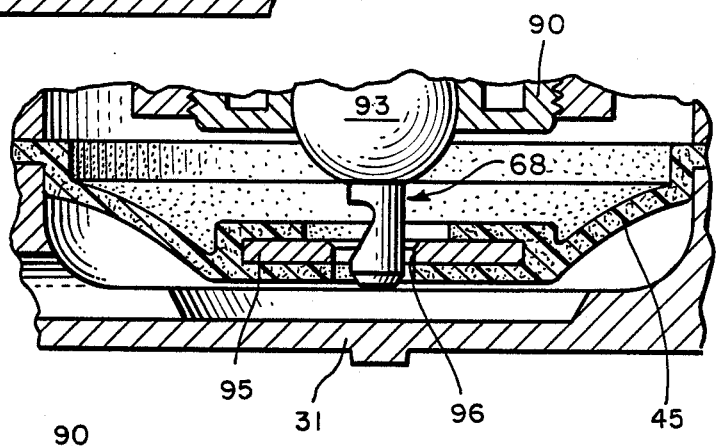
FIG. 20 is a cross-sectional view, similar to FIG. 18, showing the valve in a constant flow rate valving condition.
Figure 21:
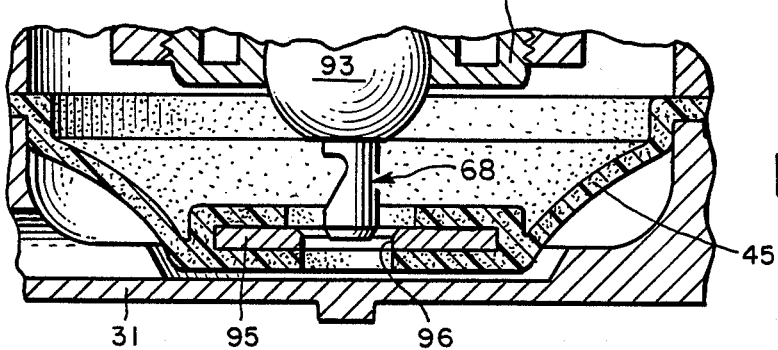
FIG. 21 is a cross-sectional view, similar to FIG. 18, showing the valve in a second constant pressure valving condition.

As shown by FIGS. 14–15, the effect of metering notch 80 is to progressively reduce the portion of orifice 70 available for fluid flow. This provides the Region II constant flow valving condition illustrated in FIG. 8. When a sudden increase in differential pressure occurs, and the pressure differential exceeds pressure $P_1$, the downward displacement of diaphragm 45 causes valve seat 67 to descend over metering portion 78 allowing flow to occur through orifice 70 only by way of metering notch 80. Since the depth of the notch decreases with increased deflection of the diaphragm, the higher flow rate ordinarily resulting from increased pressure is offset by a more restricted flow path, so that a relatively uniform rate of fluid flow occurs between the chambers despite differential pressure increases.

FIG. 9 illustrates operation of the valve in region III of FIG. 10, such as would occur when the differential pressure exceeds a predetermined pressure level $P_2$. In this condition, differential pressure displaces the diaphragm to a degree sufficient to cause valve seat 67 to move beyond the bottom portion 81 of valve stem 68 so as to allow CSF to flow past the aforesaid bottom portion and through orifice 70. Further, increases in differential pressure cause the valve seat to be further displaced away from valve stem 68 thereby further opening orifice 70 and allowing a still greater fluid flow rate. Thus, the valve operates as a pressure regulating device, increasing flow to counteract pressure increases increases, and the predetermined maximum pressure $P_2$ is maintained.

Valve closing pressure (minimum pressure level) and the point of greatest flow restriction (maximum pressure level) can be set independently by adjustment of valve closure member 69 and valve stem 68, and the length between the flow control surface 73 and the point of greatest fluid flow restriction is not a design limitation. By reason of the two adjustments, variations in physical properties of diaphragms can be accommodated.

Manufacturing techniques are less exacting and costly by reason of the cylindrical valve stem construction, wherein a single notch, which can be readily and accurately machined by conventional milling techniques provides a precision metering orifice for flow control. This avoids the multiple diameter pin constructions of previous valve designs, which could only be formed by multiple step techniques at substantial expense. Furthermore, the annular valve closure member 69, by reaason of its 360° circumferential metering surface 73, provides positive fluid control between valve closed and open states with only limited movement of diaphragm 45, thereby allowing the valve to be constructed with minimum thickness.

Conventional materials may be used in constructing pressure relief valve 12. For example, the valve stem 68, valve closure member 69 and valve seat 67 may be formed of 316 stainless steel. The housing may be formed from a biocompatible polycarbonate material and diaphragm 45 may be formed from a silicone material.

An alternate construction for a CSF pressure relief valve utilizing the novel cylindrical valve stem member is shown in FIGS. 17–21. Basically, this construction replaces the annular valve closure member of the previously described embodiment with a non-flow controlling member 90 having a threaded outer surface 91 for mounting in aperture 40, and a central aperture 92. A spherical valve closure member 93 is mounted within retaining member 90. An aperture 94 is provided in member 93 for receiving valve stem 68, which extends through this aperture and through aperture 92 in member 90.

A valve seat 95 mounted on diaphragm 45 includes an orifice 96 having inclined and parallel sidewall portions in the direction of fluid flow for coacting with valve closure member 93 and the metering portion 78 of valve stem 68 to control CSF flow in the three valving conditions previously described. FIGS. 18–21 illustrate these valving conditions which correspond to the illustrations of FIGS. 6–9.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A valve for controlling the passage of body fluids from one location in the body to another location, comprising:

a housing having first and second interior chambers;

inlet port means for establishing fluid communication between said first chamber and the one location;

outlet port means for establishing fluid communication between said second chamber and the other location;

partition means in said housing separating said first and second chambers and being movable in response to fluid pressure differential therebetween;

a valve seat forming part of said partition means and defining a fluid flow orifice to permit flow of fluid between said chambers; and a valve stem in said housing extending through said orifice to control fluid flow therethrough, said valve stem being generally cylindrical in form and including a metering notch for controlling fluid flow through said orifice, said metering notch defining a chordal surface with respect to said valve stem.

2. A valve as defined in claim 1 wherein said notch is of progressively decreasing depth along the axis of said valve stem.

3. A valve as defined in claim 1 including a valve closure member in said housing engageable with said valve seat for preventing fluid flow between said chambers in the absence of a predetermined minimum pressure differential between said chambers.

4. A valve as defined in claim 3 wherein said housing includes a first movable member to which is attached said valve closure means and which provides for adjustment thereof; and a second movable member forming a part of said valve stem means for adjustment thereof, both said first and second movable members being accessible externally of said housing for independent adjustment thereof.

5. In an intracranial pressure regulator valve adapted for transfer of cerebrospinal fluid from one location to another, said regulator valve including fluid handling chambers separated by a flexible biocompatible diaphragm which defines a valve seat having a flow metering orifice, the improvement comprising:

a valve stem in said housing extending through said orifice to control fluid flow therethrough, said valve stem being generally cylindrical in form and including a metering notch for controlling fluid flow through said orifice, said metering notch defining a chordal surface with respect to said valve stem.

6. A valve as defined in claim 5 wherein said notch is of progressively decreasing depth along the axis of said valve stem.

7. A valve for controlling the passage of body fluids from one location in the body to another location, comprising:

a housing having first and second interior chambers;

inlet port means for stabilizing fluid communication between said first chamber and the one location;

outlet port means for establishing fluid communication between said second chamber and the other location;

valving means between said first chamber and said second chamber for regulating fluid flow between said first and second chambers, said valving means including a valve closure member, a valve seat defining a flow metering orifice and a valve stem extending through said orifice and providing a first condition in which fluid flow between said first and second chambers is prevented, a second condition in which fluid flow between said first and second chambers is sufficient to maintain a first substantially constant predetermined pressure in said first chamber, a third condition in which fluid flow between said first and second chambers is of a substantially constant rate, and a fourth condition in which fluid flow between said first and second chambers is sufficient to maintain a second substantially constant predetermined pressure in said first chamber;

partition means in said housing including a diaphragm separating said first and second chambers and movable in response to the pressure differential therebetween, said valve seat being carried on said diaphragm and being operatively associated with said valve closure member and said valve stem such that the flow between said first and second chambers is sequentially conditioned by said second part from said first condition through said second and third conditions to said fourth condition whereby in response to an increasing pressure differential between fluid at the one location and fluid at the other location said valving means sequentially prevents the passage of fluids between the one location and the other location, maintains a constant fluid pressure differential between the one location and the other location, maintains desired constant rate of fluid flow between the one location and the other location, and maintains a second constant fluid pressure differential between the one location and the other location; and wherein said valve stem is generally cylindrical in form and of a lesser diameter than said metering orifice, and includes a metering notch on the surface thereof, said metering notch defining a chordal surface with respect to said valve stem for controlling fluid flow through the orifice.

8. A valve as defined in claim 7 wherein said notch is of progressively decreasing depth along the axis of said valve stem.

* * * * *